(12) United States Patent
Begemann et al.

(10) Patent No.: US 8,647,331 B2
(45) Date of Patent: Feb. 11, 2014

(54) SHAFT CONNECTOR

(75) Inventors: Malcolm Jon Simon Begemann, Velp (NL); Wimold Pieter Steven Peters, Groningen (NL)

(73) Assignee: Neurendo B.V, Groningen (NL)

( * ) Notice: Subject to any disclaimer, the term of this patent is extended or adjusted under 35 U.S.C. 154(b) by 143 days.

(21) Appl. No.: 12/949,500

(22) Filed: Nov. 18, 2010

(65) Prior Publication Data

US 2011/0118710 A1 May 19, 2011

(30) Foreign Application Priority Data

Nov. 19, 2009 (NL) .................................. 2003831

(51) Int. Cl.
  *A61B 17/00* (2006.01)
(52) U.S. Cl.
  USPC .................................................... 606/1
(58) Field of Classification Search
  USPC ......... 606/1, 130; 604/164.04, 174, 175, 264, 604/539
  See application file for complete search history.

(56) References Cited

U.S. PATENT DOCUMENTS

| | | | | |
|---|---|---|---|---|
| 4,681,103 A | * | 7/1987 | Boner et al. .................... 606/1 |
| 4,805,615 A | * | 2/1989 | Carol ............................ 606/130 |
| 4,955,891 A | * | 9/1990 | Carol ............................ 606/130 |
| 5,116,345 A | * | 5/1992 | Jewell et al. .................. 606/130 |
| 5,269,305 A | * | 12/1993 | Corol ............................ 600/429 |
| 5,320,628 A | * | 6/1994 | Ufkin ............................ 606/130 |
| 5,443,484 A | * | 8/1995 | Kirsch et al. ............. 604/164.04 |
| 5,651,771 A | * | 7/1997 | Tangherlini et al. .......... 604/158 |
| 5,720,750 A | * | 2/1998 | Koller et al. .................... 606/85 |
| 6,071,288 A | * | 6/2000 | Carol et al. ................... 606/130 |
| 6,152,933 A | * | 11/2000 | Werp et al. .................... 606/130 |
| 6,423,077 B2 | * | 7/2002 | Carol et al. ................... 606/130 |
| 6,482,182 B1 | * | 11/2002 | Carroll et al. ................. 604/174 |
| 7,217,276 B2 | * | 5/2007 | Henderson et al. ........... 606/130 |
| 7,731,695 B2 | * | 6/2010 | McFarlane ............... 604/167.06 |
| 7,842,013 B2 | * | 11/2010 | Haberland et al. ....... 604/167.03 |
| 8,182,540 B2 | * | 5/2012 | Lin et al. .................... 623/17.19 |
| 8,234,731 B2 | * | 8/2012 | Skripps ............................ 5/622 |
| 2003/0040753 A1 | * | 2/2003 | Daum et al. .................... 606/96 |
| 2009/0306501 A1 | * | 12/2009 | Flint ............................ 600/437 |
| 2010/0042111 A1 | * | 2/2010 | Qureshi et al. ................ 606/130 |
| 2010/0143858 A1 | * | 6/2010 | Okkerse et al. ................ 433/34 |
| 2012/0041472 A1 | * | 2/2012 | Tan et al. ...................... 606/200 |

FOREIGN PATENT DOCUMENTS

| WO | WO 98/17191 A1 | 4/1998 |
|---|---|---|
| WO | WO 01/78814 A1 | 10/2001 |

\* cited by examiner

*Primary Examiner* — Bill Thomson
*Assistant Examiner* — John R Downey
(74) *Attorney, Agent, or Firm* — Birch, Stewart, Kolasch & Birch, LLP

(57) ABSTRACT

A shaft connector configured to connect a shaft that has to be partly inserted through the skull of patient to the skull of the patient, the shaft connector comprising a skull connecting part, a shaft bush with a shaft clamp to fixate a shaft within the shaft bush, a bush clamping device to fixate the shaft bush relative to the skull connecting part so that a settable direction of the bush channel axis relative to the central axis is fixated as desired, an operating provision including a first and a second handle configured and arranged to be engaged by a single hand, the operating provision being configured to bring the bush clamping device from the release position in the clamping position by movement of the first handle relative to the second handle without exerting a force on the skull via the skull connecting part.

24 Claims, 5 Drawing Sheets

SHAFT CONNECTOR

FIELD

The invention relates to a shaft connector for connecting a shaft that has to be partly inserted through the skull of patient to the skull of the patient.

BACKGROUND

U.S. Pat. No. 4,681,103 discloses a shaft connector configured to connect a shaft that has to be partly inserted through the skull of patient to the skull of the patient. The shaft connector has an adaptor housing that includes external screw thread with which the adaptor housing can be mounted in a hole that has been drilled in the skull of a patient. The shaft connector also includes a shaft bush or probe socket with a swivel ball. The probe socket defines a bush channel that extends along a bush channel axis. A set screw is provided to fixate a shaft within the probe socket. A clamp plate having a central hole with a diameter that is smaller than that of the swivel ball is arranged in the adaptor housing. A locking ring having external screw thread that engages internal screw thread on the adapter housing co-operates with the clamp plate so that the clamp plate can be pressed downward to force the clamp plate against the swivel ball thereby locking it in place between the adaptor housing and the clamp plate. If the locking ring is loose, the probe socket can swivel within the adaptor housing.

WO-98/17191 discloses a similar device. In this case the connection between the adaptor housing and the skull is effected by means of hooks on distal ends of flexible legs that are connectable to the adaptor housing. The hooks engage a hole drilled in the skull on the inside of the skull. The adaptor housing can be connected to the skull by tightening a first locking ring having internal screw thread that engages external screw thread on the adaptor housing. A second locking ring with external screw thread that engages internal screw thread can be used to fixate a shaft bush having a swivel ball into a desired directional position in the adaptor housing.

SUMMARY OF THE INVENTION

A disadvantage of the known devices is that to fixate the swivel ball inside the adaptor housing a locking ring with screw thread that engages the adaptor housing has to be tightened. When one has only one hand available, tightening the locking ring will result in exerting a force on the skull via the adaptor housing. This may change the position of the adaptor housing and with that of the probe socket relative to the skull and the brain tissue. Such an inadvertent position change is highly undesirable because it may lead to brain damage when a shaft is inserted into the brain. Additionally the connection between the adaptor housing and the skull is vulnerable and possible varying forces that may deteriorate the connection should preferably be prevented.

The present invention is directed to a shaft connector in which these disadvantages are alleviated.

To that end the invention provides a shaft connector that is configured to connect a shaft that has to be partly inserted through the skull of patient to the skull of the patient, wherein the shaft connector comprises a skull connecting part having a proximal end and a distal end. The skull connecting part includes a skull connecting provision and an inner wall that bounds a skull connecting part channel that extends along a central axis and that has a distal channel end. The skull connector also comprises a shaft bush that includes a shaft bush wall defining a bush channel that extends along a bush channel axis. Further, the shaft connector includes a bush clamping device that is arranged in the skull connecting part, that has a clamping position and a release position, the bush clamping device in the clamping position being configured to fixate the shaft bush relative to the skull connecting part so that a direction of the bush channel axis relative to the central axis, which direction may be varied within a range of directions in the release position of the bush clamping device, is fixated as desired. An operating provision of the shaft connector is configured to engage the bush clamping device and to move the bush clamping device between the clamping position and the release position. In a first aspect the operating provision includes at least a first handle and a second handle. The first and the second handles are configured and arranged to be engaged by a single hand and the operating provision is configured to bring the bush clamping device from the release position in the clamping position by movement of the first handle relative to the second handle without exerting a force on the skull via the skull connecting provision.

Therefore, the invention provides a shaft connector according to claim 1.

By virtue of the fact that the shaft bush may be fixated in a desired direction by engagement of the first and the second handle with a single hand without exerting a force on the skull connecting provision, a very user friendly shaft connector is provided. The stability of the connection between the skull and the shaft connecting part is not brought into danger because of forces that are exerted on that connection during fixating the shaft bush relative to the skull connecting part. Thus the position of the skull connecting part relative to the skull, which position at least partly defines the position of the shaft within the skull which is very precarious, is maintained unaffected and stable. Optionally a third handle may be provided as will be elucidated in the detailed description.

In an embodiment, the rotational position of the first handle and the second handle relative to the skull connecting part may be settable without changing the position of the first handle relative to the second handle.

This embodiment facilitates that the surgeon may position the handles so relative to his own working position and other instruments that operating the handles is easy for him.

In an embodiment, the shaft bush of the shaft connector may include a shaft clamp that is configured to fixate a shaft within the shaft bush 50. The shaft clamp of the shaft bush may include a first shaft clamp handle and a second shaft clamp handle. The first and the second shaft clamp handles may be configured and arranged to be engaged by a single hand and the shaft clamp may be configured to bring shaft clamp from the release position in the clamping position by movement of the first shaft clamp handle relative to the second shaft clamp handle without exerting a force on the skull via the skull connecting provision.

By virtue of the fact that the shaft may be fixated in a desired position relative to the shaft bush by engagement of the first clamp handle and the second clamp handle with a single hand without exerting a force on the skull via the skull connecting provision, a very user friendly shaft connector is provided. Consequently, the position of the skull connecting part relative to the skull, which position as stated before at least partly defines the position of the shaft within the skull which is very precarious, is maintained unaffected and stable. It should be noted that the novel shaft clamp may also be applied in a shaft connector that does not have the novel operating provision with the first and the second handle. Optionally a third clamp handle may be provided as will be elucidated in the detailed description.

To facilitate the possibility of positioning the shaft clamp handles in a favorable position relative to the surgeon and other instruments, in an embodiment of the shaft connector the rotational position of the first shaft clamp handle and the second shaft clamp handle relative to the shaft bush may be settable without changing the position of the first shaft clamp handle relative to the second shaft clamp handle.

In an embodiment, the skull connection provision may include a substantially cylindrical part that extends proximally from the distal end of the skull connecting part. A stop surface may be provided at a proximal end of the substantially cylindrical part and may extend substantially perpendicular to the central axis. The skull connecting part may further include an outer surface wall that is circular symmetric around the central axis and that extends from a proximal end of the cylindrical part substantially parallel to the central axis in the proximal direction and diverges radial outwardly, thus providing a concave transition zone that is configured to accommodate skin on the skull that surrounds the hole in which the skull connecting part may be mounted. The stop surface may engage the outer surface of the skull and thus provide a large, stability providing bearing surface. The transition zone with the special contour provides space for the skin that surrounds the hole in the skull. Thus, a minimal amount of skin has to be removed which is important in view of minimizing the cicatrix mark that remains after the surgery. The aspects of this embodiment may also be applied in a skull connector that does not have the features of the first and the second handle in the operating provision.

In yet another embodiment, the shaft bush of the shaft connector may include a substantially spherical distal shaft bush end that is pivotably accommodated in the skull connecting part so that the shaft bush is pivotable relative to the skull connecting part. In order to obtain a maximum range of pivot angles relative to the central axis of the skull connecting part in combination with a minimal diameter of the hole that has to be drilled in the skull, in the present embodiment the substantially spherical distal shaft bush end may be positioned adjacent the distal channel end of the skull connecting part so that in a mounted position of the skull connecting part in a hole in a skull, the substantially spherical distal shaft bush end is positioned below an outer surface of skull. The aspects of this embodiment may also be applied in a skull connector that does not have the features of the first and the second handle in the operating provision.

Other aspects are described in the dependent claims and will be elucidated in the detailed description.

DETAILED DESCRIPTION

Figure 1:
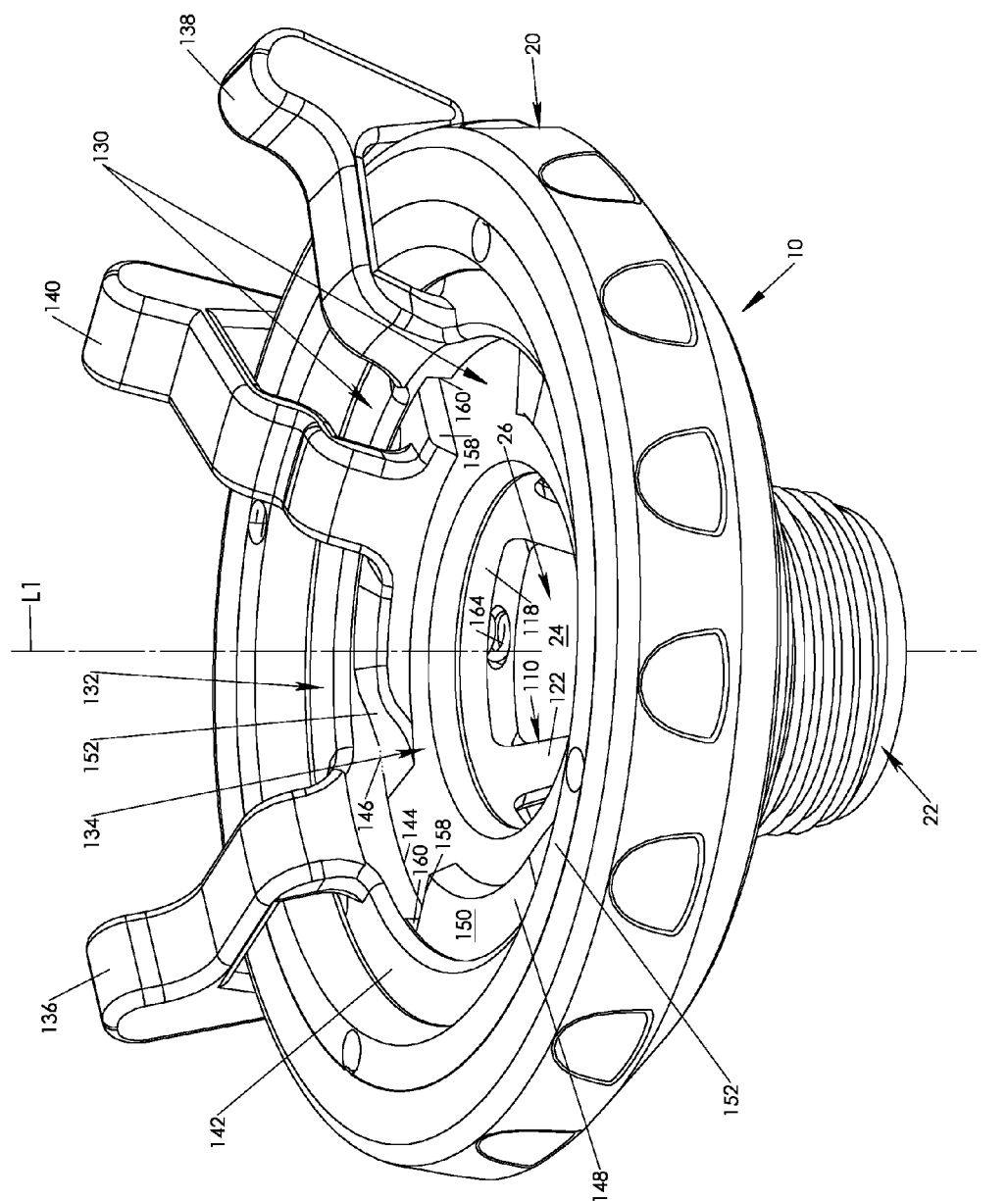
FIG. 1 shows in perspective view an example of an embodiment of a skull connector in which the shaft bush with the shaft clamp are not depicted for reasons of clarity.

In its most general terms shaft connector 10 is disclosed that is configured to connect a shaft that has to be partly inserted through the skull of patient to the skull of the patient. The shaft may, for example, be a tool, an endoscope, a catheter, a drain or a trocar. The figures show examples of the various embodiments that will be described hereafter.

The embodiments of the shaft connector 10 have in common that they all comprise a skull connecting part 20 having a proximal end and a distal end. The skull connecting part 20 includes a skull connecting provision 22 and an inner wall 24 that bounds a skull connecting part channel 26 that extends along a central axis L1 and that has a distal channel end 26a. The shaft connector 10 also comprises a shaft bush 50. The shaft bush 50 includes a shaft bush wall 52 defining a bush channel 54 that extends along a bush channel axis L2. Next, the shaft connector comprises a bush clamping device 110 that is arranged in the skull connecting part 20. The bush clamping device 110 has a clamping position and a release position. In the clamping position the bush clamping device is configured to fixate the shaft bush 50 relative to the skull connecting part 20 so that a direction of the bush channel axis L2 relative to the central axis L1, which direction may be varied within a range of directions in the release position of the bush clamping device 110, is fixated as desired. The shaft connector 10 also comprises an operating provision 130 configured to engage the bush clamping device 110 and to move the bush clamping device 110 between the clamping position and the release position.

In an embodiment, of which two different examples are shown in FIGS. 1-3 and 5, the operating provision 130 may include at least a first handle 136 and a second handle 140. The first and the second handles 136, 140 may be configured and arranged to be engaged by a single hand and the operating provision 130 may be configured to bring the bush clamping device 110 from the release position in the clamping position by movement of the first handle 136 relative to the second handle 140 without exerting a force on the skull via the skull connecting provision 22. This is advantageous in that the stability of the connection between the shaft connector 10 and the skull is maintained. Thus the position of a shaft that is inserted through the shaft bush 50 into the brain of the patient is also stable. This is of crucial importance. Because the surgeon can operate the operating provision 130 with a single hand, the skull connector is very user friendly. The surgeon has his other hand freely available for manipulating other instruments or, for example, the shaft of which he wants to fixate its position.

In an embodiment, of which two different examples are shown in FIGS. 1-3 and 5, the rotational position of the first handle 136 and the second handle 140 relative to the skull connecting part 20 may be settable without changing the position of the first handle 136 relative to the second handle 140. This embodiment facilitates that the handles 136, 140 may be freely rotated and thus be brought into a position that is easily accessible for the surgeon.

In an embodiment, of which examples are shown in FIGS. 1-3 and 5, the operating provision 130 may include a third handle 138. The first and the second handles 136, 140 and the third handle and the second handles 138, 140 may be configured and arranged to be engaged in pairs by a single hand and the operating provision may be configured to bring the bush clamping device 110 from the release position in the clamping position by movement of the first handle 136 relative to the second handle 140 without exerting a force on the skull via the skull connecting provision 22, and to bring the bush clamping device 110 from the clamping position in the release position by movement of the third handle 138 relative to the second handle 140 without exerting a force on the skull via the skull connecting provision 22. An embodiment with three handles 136, 138, 140 has the advantage that both for releasing and for clamping a press movement may be used. Pressing together two handles is an operation that can be easily performed with a single hand, for example, by engaging one handle with a thumb and the other one with the index finger.

Also in the embodiment with the three handles 136, 138, 140, the rotational position of the first handle 136, the second handle 140 and the third handle 138 relative to the skull connecting part 20 may be settable without changing the position of the first handle 136, the second handle 140 and the third handle 138 relative to each other.

In an embodiment, of which two examples are shown in FIGS. 1-3 and 5, the second handle 140 may be positioned between the first handle 136 and the third handle 138.

In an embodiment, of which two examples are shown in FIGS. 1-3 and 5, the operating provision 130 may include a first operating part 132 that is connected to the skull connecting part 20 that carries the first handle 136. The operating provision 130 may also include a second operating part 134 that is connected to the skull connecting part 20 and that carries the second handle 140. The first operating part 132 may be moveable relative to the second operating part 134 from a clamping position, that is associated with the clamping position of the operating provision 130, to the release position, that is associated with the release position of the operating provision 130, and vice versa.

In an embodiment, of which two examples are shown in FIGS. 1-3 and 5, the first operating part 132 also carries the third handle 138. The movability of the first operating part 132 relative to the second operating part 134 may involve a rotation around the central axis L1.

In that example, both the first operating part 132 and the second operating part 134 are also simultaneously rotatable around the central axis L1 relative to the skull connecting part 20 so that the rotational position of the handles relative to the skull connecting part 20 is settable. Thus the handles 136, 138, 140 can be positioned so that the surgeon can readily engage the handles.

Figure 3:
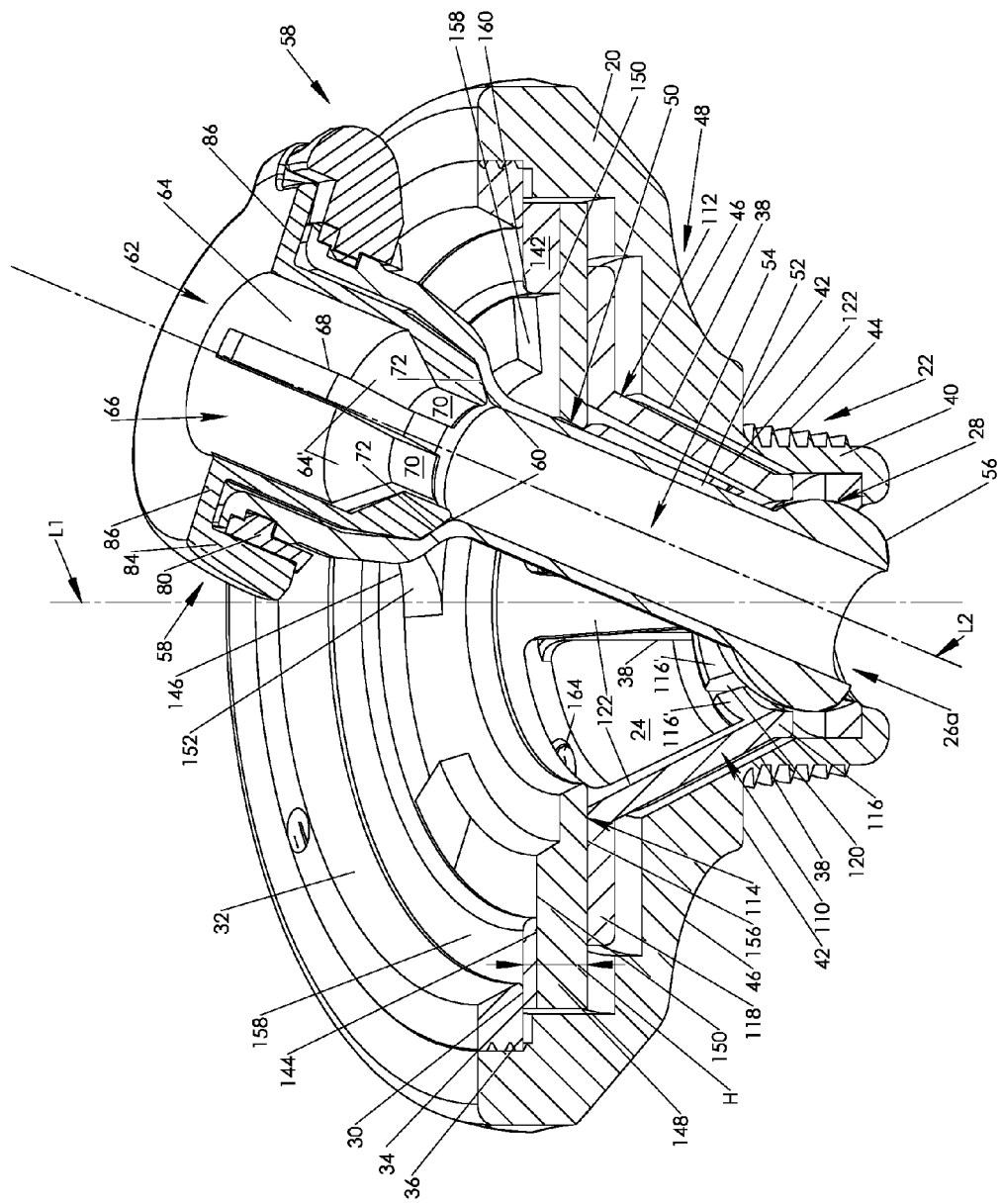
FIG. 3 shows a perspective cross section of the example of the embodiment of FIGS. 1 and 2 in which the shaft bush with the shaft clamp are present.

In an embodiment, of which the features to be described are clearly visible in the example that is shown in FIG. 3, the first operating part 132 may include a first ring 142 that extends in a plane that is perpendicular to the central axis L1. The first ring 142 has a central ring axis that coincides with the central axis L1 and has a first contact surface 144 with a first sloping section 146. The second operating part 134 includes a second ring 148 that extends in a plane that is perpendicular to the central axis L1. The second ring 148 has a central ring axis that coincides with the central axis L1 and has a second contact surface 150 with a second sloping section 152. In fact, both rings 142 and 148 each include in the example shown three sloping sections 146, 152. Both the first contact surface 144 and the second contact surface 150 each include a stop surface 160, 162, in fact three stop surfaces that limit the rotation of the two rings 142, 148 relative to each other. The first contact surface 144 contacts the second contacting surface 150. The first ring 142 and the second ring 148 are superimposed onto each other to form a ring set having a variable ring set height H. The ring set has a flat bottom surface 156 that is in contact with the bush clamping device 110. The ring set has a flat top surface 158 that is positioned under a ridge 30 of the skull connecting part 20. The first sloping section 146 and the second sloping section 152 are positioned so relative to each other that these two sloping sections co-operate upon rotation of the first ring 142 relative to the second ring 148 thereby increasing or decreasing the ring set height H.

In an embodiment, the first and the second sloping sections 146, 152 may each include more than two stages, for example, three stages. A first stage that is associated with a release position, an intermediate second stage that is associated with a position in which movement of the shaft bush 50 is possible but inhibited by a friction force, and a second stage that is associated with the clamping position. In another embodiment, the sloping section 146, 152 may include a plurality of stages thus providing a sort of a ratchet for exerting variable clamping forces.

Figure 2:
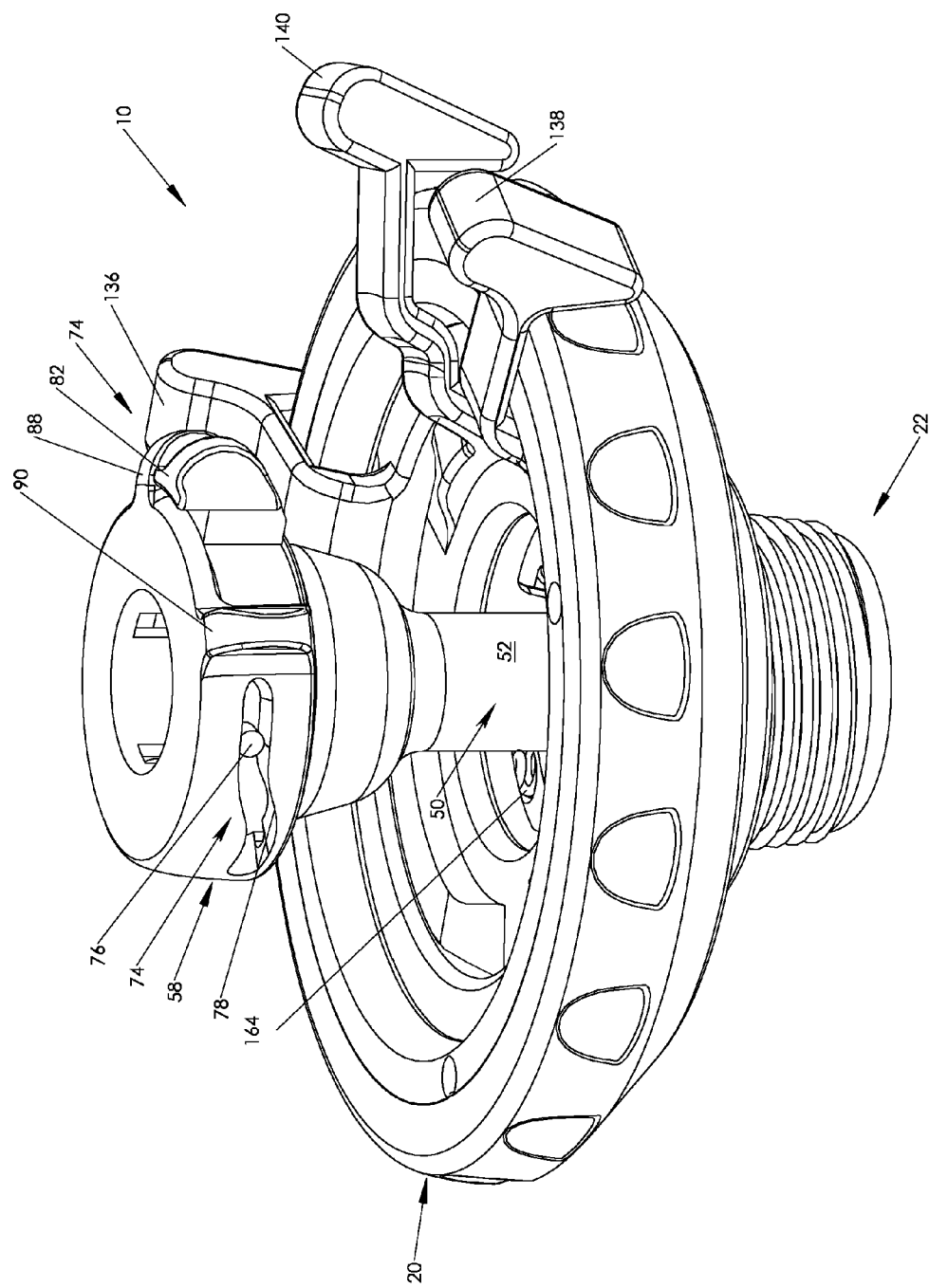
FIG. 2 shows in perspective view from a slightly different angle the example of FIG. 1 in which the shaft bush with the shaft clamp are present.

In an embodiment, of which an example is shown in FIGS. 1-3, the ridge 30 of the skull connecting part 20 is part of a ridge ring 32 having outer screw thread 34 that engages inner screw thread 36 of the skull connecting part 20 so that the distance between the ridge 30 and the seat 28 is settable by rotation of the ridge ring 32. By virtue of the ridge ring 32, the skull connecting part 20 may be releasable from a mold in which the skull connecting part 20 may be manufactured by means of, for example, injection molding. By virtue of the separate ridge ring 32, any manufacturing tolerance may be compensated for by turning the ridge ring 32 in such a position that the height between the ridge ring 32 and an upper side the bush clamping device 110 is as desired.

Figure 4:
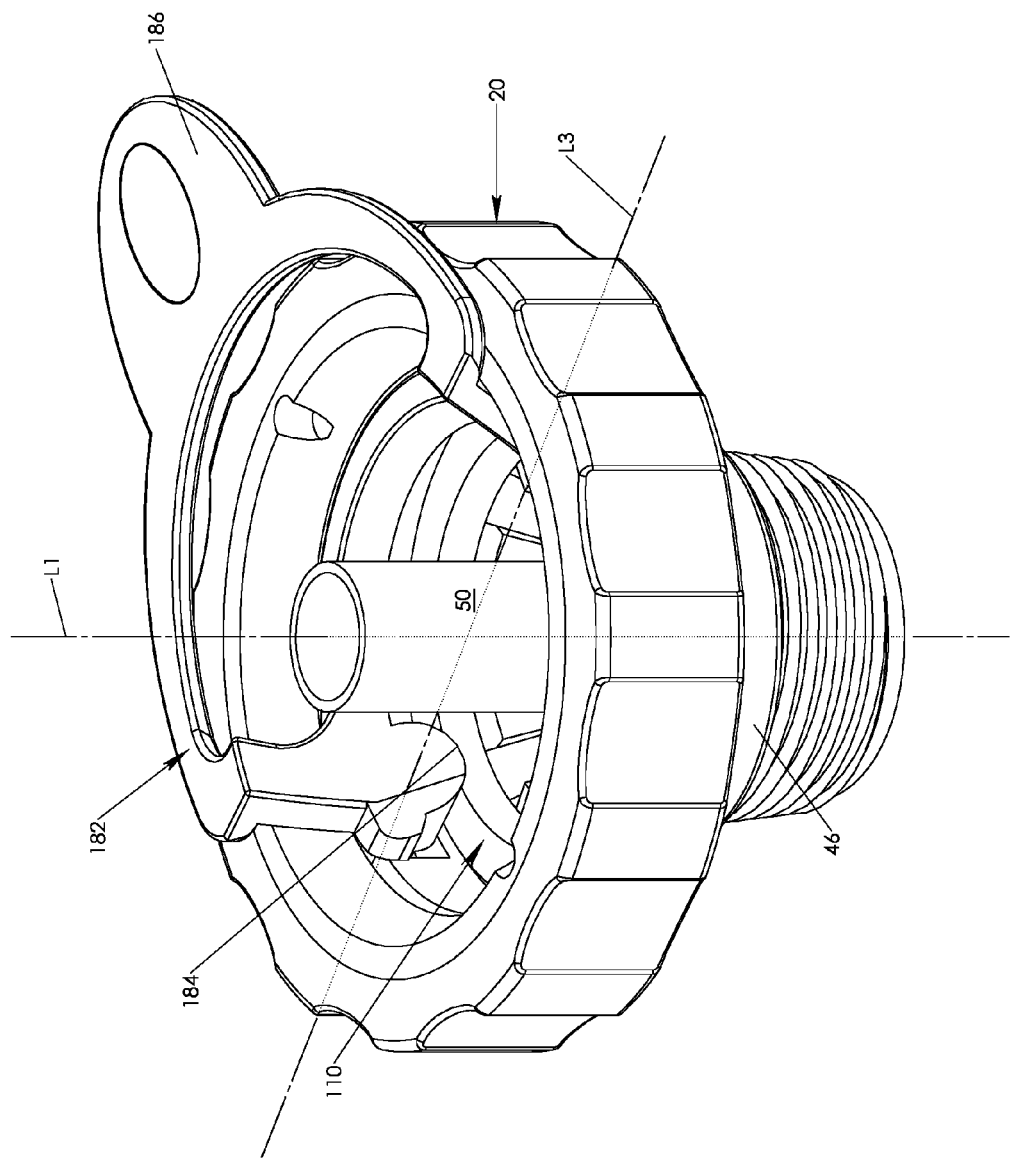
FIG. 4 shows a perspective view from an example of a second embodiment.

In an alternative embodiment, of which an example is shown in FIG. 4, the shaft connector includes a first operating part 182 that carries the first handle 186 and that is connected to the skull connecting part 20 and pivotable along a pivot axis L3 that crosses and extends substantially perpendicular to the central axis L1. The first operating part 182 includes at least one cam surface 184—in the example shown in FIG. 4 two cam surfaces 184—that has an eccentric contour relative to the pivot axis L3 and that engages the bush clamping device 110. The pivot position of the first operating part 182 along the pivot axis L3 relative to the skull connecting part 20 is settable by operating the first handle 186. An radial outwardly extending flange could be provided on the skull connecting part 20 to form a second handle that can, for example, be engaged by the index finger while the first handle 186 is engaged by the thumb of the same hand of the surgeon to fixate the shaft bush 50 in the desired angular position relative to the skull connecting part 20.

In an embodiment, of which an example is shown in FIGS. 1-3, the skull connecting part 20 may include a seat 28 adjacent the distal channel end 26a. The shaft bush 50 may include a substantially spherical distal shaft bush end 56 having a proximal side and a distal side. The bush clamping device 110 may include a bush clamp provision 112 that engages the proximal side of the substantially spherical distal shaft bush end 56 in the clamping position and presses the spherical distal shaft bush end 56 with the distal side thereof against the channel seat 28. The bush clamping device 110 may further have an operating provision engagement part 114 that is fixedly connected to the bush clamp provision 112. The bush clamping device 110 of that embodiment is movable in the direction of the central axis L1 between the clamping position and the release position.

In an embodiment, the skull connector 10 may include a biasing member configured to bias the bush clamping device to the release position. An example of such a biasing member is shown in FIG. 2. The example of the biasing member is a push spring 164 that is positioned between the bush clamping device 110 and the inner wall 24 of the skull connecting part 20. The spring 164 urges the bush clamping device 110 away from the seat 28 when the operating provision is brought form the clamping position to the release position. It is clear that the biasing member may be embodied in alternative manners. For example, the biasing member may be embodied as a ring of compressible material between the bush clamping device 110 and the skull connecting part 20.

In an embodiment, of which an example is shown FIGS. 1-3, the bush clamp provision 112 includes a lower ring 116 and the operating provision engagement part 114 includes an upper ring 118 having a top engagement surface that is engaged by the operation provision 130. The upper ring 118 and the lower ring 116 are fixedly connected to each other via spokes 122. The inner wall 24 of the shaft connecting part 20 may include indentations 38 for accommodating the spokes 122. Thus the diameter of the skull connecting part 20, especially adjacent the proximal end of the skull connecting provision 22 may be kept minimal while simultaneously an optimally large pivot range for the shaft bush 50 may be provided. Radially between the indentations 38 enough wall material is present to provide sufficient strength to the skull connecting part 20. At the position of the indentations the wall of the skull connecting provision may be very thin so that the angles over which the shaft bush 50 may be tilted relative to the central axis L1 are maximal.

In an embodiment, of which an example is shown in FIG. 3, the lower ring 116 may include interruptions 120 so that lower ring segments 116' are provided that are each connected with at least one spoke 122. The ring segments 116' have some radial movement possibility so that in the clamping position each ring segment 116' may be optimally inserted between the inner wall 24 and the spherical distal shaft bush end 56 so that each segment may contribute to exerting a clamping force on the spherical distal shaft bush end 56.

In an embodiment, the ring 116 or the ring segments 116' may have a tapering converging configuration when viewed in the direction of the central axis L1 form the proximal end to the distal end. When moved towards the seat 28, the ring or the ring segments 116 are wedged between the inner wall 24 and the substantially spherical distal shaft bush end 56 thus fixating the spherical distal shaft bush end 56 and with that the shaft bush 50 in its desired position.

In an alternative embodiment, the spokes 122 may be configured to bias the ring segments 116' outwardly in a radial direction of the ring 116. The inner wall 24 at the level of the lower ring 116 may have a tapering configuration so that when moving from the release to the clamping position, the ring segments 116' are moved from a position in which the tapering inner wall has a larger diameter to a position in which the tapering inner wall has a smaller diameter whereby the ring segments 116' are forced to move inwardly in a radial direction. When moving from the clamping position to the release position, the ring segments 116' are moved from a position in which the tapering inner wall has a smaller diameter to a position in which the tapering inner wall has a lager diameter whereby the ring segments 116' move outwardly in the radial direction by the bias force of the spokes 122.

Figure 5:
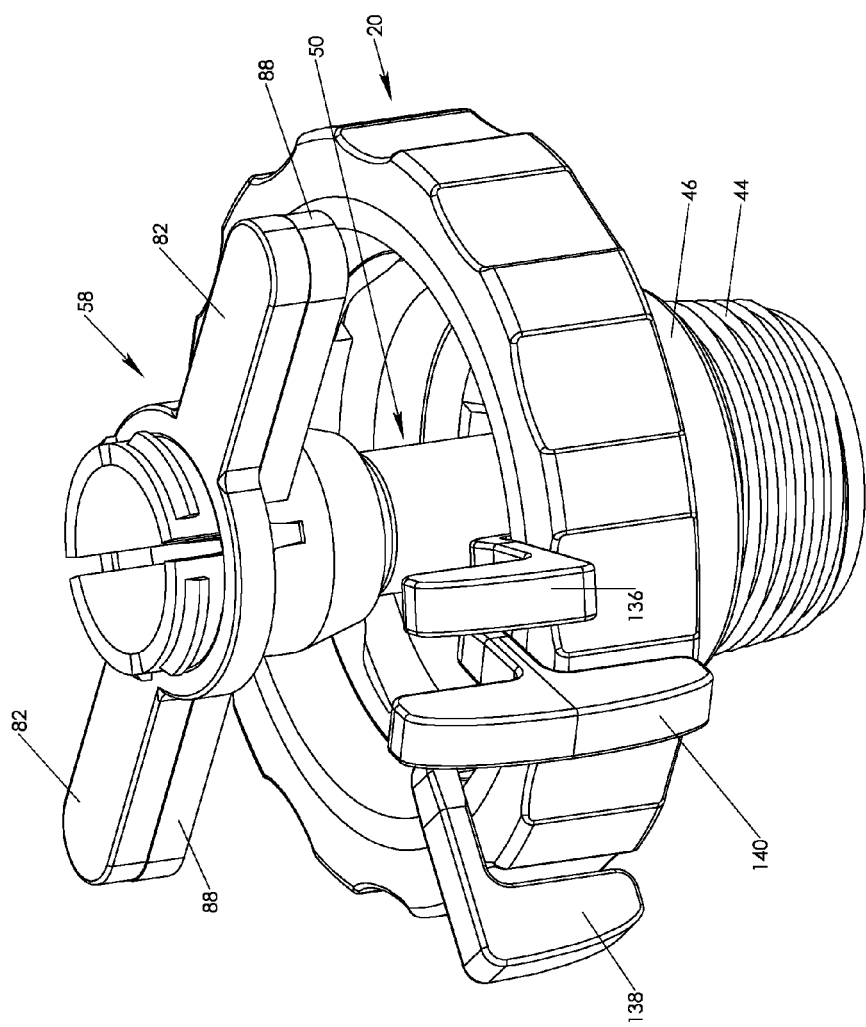
FIG. 5 shows a perspective view from an example of a third embodiment.

In an embodiment of the shaft connector 10, the shaft bush 50 may include a shaft clamp 58 that is configured to fixate a shaft within the shaft bush 50. An embodiment of the shaft clamp 58 of the shaft bush 50 of which two examples are shown in FIGS. 2, 3 and 5, may include a first shaft clamp handle 82 and a second shaft clamp handle 88. The first and the second shaft clamp handles 82, 88 are configured and arranged to be engaged by a single hand and the shaft clamp 58 is configured to bring shaft clamp 58 from the release position in the clamping position by movement of the first shaft clamp handle 82 relative to the second shaft clamp handle 88 without exerting a force on the skull via the skull connecting provision 22. In an embodiment, of which an example is shown in FIGS. 2 and 3, the movement of the first shaft clamp handle 82 relative to the second shaft clamp handle 88 may be a rotational movement around the shaft bush axis L2 to bring the shaft clamp 58 from the clamping position to the release position and vice versa. In an alternative embodiment, of which an example is shown in FIG. 5, the first shaft clamp handle 82 may be moved in the direction of the shaft bush axis L2 relative to the second shaft clamp handle 88 to bring the shaft clamp 58 from the clamping position to the release position and vice versa. In the example of FIG. 5, the external diameter of the slitted bush may have an axial portion with a large outer diameter and an axial portion with a small outer diameter relative to the large outer diameter. When the ring, that carries the first shaft clamp handles 82, is positioned over the portion with the small outer diameter, the shaft clamp 58 is in the release position. When that ring is positioned over the portion with the large outer diameter, the bush segments are pressed in a radial inward direction and the shaft clamp 58 is in the clamping position.

In an embodiment, the rotational position of the first shaft clamp handle 82 and the second shaft clamp handle 88 relative to the shaft bush 50 may be settable without changing the position of the first shaft clamp handle 82 relative to the second shaft clamp handle 88. That is advantageous because the surgeon can than position the handles 82, 88 optimally relative to him- or herself and relative to the patient.

In yet another embodiment, of which an example is shown in FIGS. 2 and 3, the shaft clamp 58 may include a third shaft clamp handle 90. The first and the second shaft clamp handles 82, 88 and alternatively the first and the third shaft clamp handles 82, 90 are configured and arranged to be engaged in pairs by a single hand. In that embodiment the shaft clamp 58 is configured to bring the shaft clamp 58 from the release position in the clamping position by movement of the first handle 82 relative to the second handle 88 without exerting a force on the skull via the skull connecting provision 22, and to bring the shaft clamp 58 from the clamping position in the release position by movement of the third shaft clamp handle 90 relative to the first shaft clamp handle 82 without exerting a force on the skull via the skull connecting provision 22. Also in the embodiment with three shaft clamp handles 82, 88, 90 it is for the same reasons as mentioned above in relation to the embodiment with the two shaft clamp handles advantageous when the rotational position of the first shaft clamp handle 82, the second shaft clamp handle 88 and the third shaft clamp handle 90 relative to the shaft bush 50 is settable without changing the position of the first handle 136, the second handle 140 and the third handle 138 relative to each other.

When, as is the case in the example of FIGS. 2 and 3, the first shaft clamp handle 82 is positioned between the second shaft clamp handle 88 and the third shaft clamp handle 90, the shaft clamp 58 may be brought from the clamping position to the release position as well as from the release position to the clamping position via a press movement. Exerting a force by pressing on two handles is easy because it can be easily done with a single hand by engaging a pair of handles 82, 88 or alternatively a pair of handles 82, 90 between the index finger and the thumb. The other hand thus remains available for other tasks, for example holding the shaft that has to be fixated.

As shown in the example of FIGS. 2 and 3, the shaft clamp 58 may include an inner tapering wall part 60 with a diminishing diameter that is defined by the shaft bush wall 52 adjacent the proximal end of the shaft bush 50. The shaft clamp 58 may include a clamp bush 62 with a clamp bush wall 64 defining a clamp bush channel 66 that extends along bush channel axis L2. The clamp bush wall 64 may include slits 68 that extend substantially parallel to the bush channel axis L2. A distal end of the clamp bush wall 64 defines shaft clamping segments 64' that are bounded by the slits 68. The clamping segments 64' have radial inwardly directed clamping surfaces 70 that are configured to engage a shaft. A radial outwardly directed clamp bush wall part 72 at the distal end of the clamp bush wall 64 co-operates with the inner tapering wall part 60. The clamp bush 62 is axially moveable within the shaft bush wall 52. A clamp bush operating provision 74 is provided to control the axial position of the clamp bush 62 relative to the shaft bush wall 52 and includes at least the first and the second shaft clamp handle 82, 88.

When the clamp bush 62 is pressed by the clamp bush operating provision 74 into the tapering wall part 60, the clamping segments 64' are forced in a radial inward direction. The clamping surfaces 70 are then pressed against the shaft and fixate the shaft relative to the shaft bush 50. When the clamp bush 62 is withdrawn by the clamp bush operating provision 74 from the tapering wall part 60, the clamping segments 64' may bias in a radial outward direction, thereby releasing the shaft that was previously fixated by the clamping surfaces 70 of the clamping segments 64'.

The clamp bush operating provision 74 may include a cam notch 76 that is axially fixed relative to the shaft bush wall 52. That embodiment of the clamp bush operating provision 74 also includes a cam surface 78 that is part of the clamp bush 62 and that is configured to co-operate with the cam notch 76. A rotation of the clamp bush 62 relative to the cam notch 76 results in a axial movement of the clamp bush 62. The cam notch 76 may be part of a notch ring 80 that is connected to the shaft bush wall 52 so that it is axially fixed relative to the shaft bush wall 52 and rotatable around the shaft bush wall 52. The first shaft clamp handle 82 may also be connected to the notch ring 80. A clamp bush skirt 84 that extends parallel to the clamp bush wall 64 and that is connected to the clamp bush wall via a connecting flange 86 may be provided to carry the cam surface 78 and the second shaft clamp handle 88 and, if present, also the third clamp handle 90. By virtue of the notch ring 80 and the clamp bush 62, the first, second and optional third clamp bush handle may be rotated without rotating the shaft bush wall 52 and without movement of the shaft clamp handles 82, 88, 90 relative to each other.

Turning now again to the skull connecting part 20. The skull connection provision 22 may include in an embodiment a substantially cylindrical part 40 extending proximally from the distal end of the skull connecting part 20. A stop surface 42 may be present at a proximal end of the substantially cylindrical part 40 and extend substantially perpendicular to the central axis L1. The stop surface 42 may provide a stable support surface that engages an outer surface of the skull that bounds the hole that has been drilled in the skull. Also, the stop surface 42 provides a well-defined indication in relation to the extent to which the skull connecting part 20 has to be inserted into the drilled hole. The cylindrical part 40 may carry outer screw thread 44 that is configured to engage the hole in the skull. The screw thread 44 may be a tapering screw thread 44. In an alternative embodiment the cylindrical part 40 may include flexible legs with radial outwardly extending hooks on the distal ends thereof that engage an inner side of the skull bounding the hole in the skull. An example of such a connecting provision is described in US WO-98/17191.

In an embodiment, of which examples are shown in FIGS. 1-5, the skull connecting part 20 may include an outer surface wall 46 that is circular symmetric around the central axis L1 and that extends from a proximal end of the cylindrical part 40 substantially parallel to the central axis L1 in the proximal direction and diverges radial outwardly, thus providing a concave transition zone 48 that is configured to accommodate skin on the skull that surrounds the hole in which the skull connecting part 20 may be mounted. Such a concave transition zone 48 provides the advantage that a minimum amount of skin has to be removed from the skull, thus minimizing the scar mark on the skull after the operation. Preferably, the radial diverging is gradually so that a smooth transition zone 48 is obtained.

In an embodiment, of which examples are shown in all the figures, the shaft bush includes a substantially spherical shaft bush end 56 that is pivotally accommodated in the skull connecting part 20 so that the shaft bush 50 is pivotable relative to the skull connecting part 20. In such an embodiment, it is advantageous when the substantially spherical distal shaft bush end 56 is positioned adjacent the distal channel end 26a of the skull connecting part 20, so that in a mounted position of the skull connecting part 20 in a hole in a skull, the substantially spherical distal shaft bush end 56 is positioned below an outer surface of skull. In such a configuration, it is possible to provide a maximum range of angles over which the direction of the shaft bush channel axis L2 may be varied relative to the central axis L1 and that in combination with a minimum hole diameter in the skull of the patient. In an embodiment that has a substantially cylindrical part 40 extending from the distal end of the skull connecting part 20, such a configuration may be obtained by positioning the seat 28 at a distal end of the cylindrical part 40 and by positioning the substantially spherical distal shaft bush end 56 in the cylindrical part 40.

The various features described in combination for certain embodiments may be applied separate from each or in other combinations so as to form other embodiments.

The priority document included some additional claims that are repeated hereunder as clauses:

11. The shaft connector according to clause 10 (now claim 10), wherein the ridge (30) of the skull connecting part (20) is part of a ridge ring (32) having outer screw thread (34) that engages inner screw thread (36) of the skull connecting part (20) so that the distance between the ridge (30) and the seat (28) is settable by rotation of the ridge ring (32).

15. The shaft connector according to clause 14 (now claim 13), the inner wall (24) of the shaft connecting part (20) including:
    indentations (38) for accommodating the spokes (122).

16. The shaft connector according to clause 14 or 15 (now claim 13 and clause 15), the lower ring (116) including:
    interruptions (120) so that lower ring segments (116') are provided that are each connected with at least one spoke (122).

17. The shaft connector according to any one of clause 14-16 (now claim 13 and clauses 15-16), the lower ring (116) having a tapering converging configuration when viewed from in the direction of the central axis (L1) the proximal to the distal end skull connecting part (20) so that in a clamping position of the bush clamping device (110), the lower ring (116) is wedged between the inner wall (24) and the substantially spherical shaft bush end (56) thus fixate the spherical shaft bush end (56) in its position.

20. The shaft connector according to clause 19 (now claim 15), wherein the rotational position of the first shaft clamp handle (82) and the second shaft clamp handle (88) relative to the shaft bush (50) is settable without changing the position of the first shaft clamp handle (82) relative to the second shaft clamp handle (88).

23. The shaft connector according to clauses 21 or 22 (now claim 16 or 17), wherein the first shaft clamp handle (82) is positioned between the second shaft clamp handle (88) and the third shaft clamp handle (90).

27. The shaft connector according to clause 26 (now claim 20), the third shaft clamp handle (90) being connected to the clamp bush skirt (84).

It will be apparent to those having ordinary skill in the art that various modifications and variations can be made to the shaft connector as disclosed herein. Other embodiments will be apparent to those having ordinary skill in the art from consideration of the specification. It is intended that the specification and examples are considered as exemplary only. Other aspects, features and advantages will be apparent upon an examination of the attached drawings and appended claims.

The invention claimed is:

1. A shaft connector configured to connect a shaft that has to be partly inserted through the skull of patient to the skull of the patient, the shaft connector comprising:
   a skull connecting part having a proximal end and a distal end, the skull connecting part including:
      a skull connecting provision;
      an inner wall that bounds a skull connecting part channel that extends along a central axis and that has a distal channel end;
   a shaft bush that includes:
      a shaft bush wall defining a bush channel that extends along a bush channel axis;
   a bush clamping device that is arranged in the skull connecting part, that has a clamping position and a release position, the bush clamping device in the clamping position being configured to fixate the shaft bush relative to the skull connecting part so that a direction of the bush channel axis relative to the central axis, which direction may be varied within a range of directions in the release position of the bush clamping device, is fixated as desired;
   an operating provision configured to engage the bush clamping device and to move the bush clamping device between the clamping position and the release position, the operating provision including at least:
      a first stage associated with the release position;
      a second stage associated with the clamping position;
      a first handle; and
      a second handle;
   the first and the second handles being configured and arranged to be engaged by a single hand and the operating provision being configured to bring the bush clamping device from the release position in the clamping position by movement of the first handle relative to the second handle,
   wherein the first stage and the second stage have different heights with respect to the skull connecting provision.

2. A shaft connector configured to connect a shaft that has to be partly inserted through the skull of patient to the skull of the patient, the shaft connector comprising:
   a skull connecting part having a proximal end and a distal end, the skull connecting part including:
      a skull connecting provision;
      an inner wall that bounds a skull connecting part channel that extends along a central axis and that has a distal channel end;
   a shaft bush that includes:
      a shaft bush wall defining a bush channel that extends along a bush channel axis;
   a bush clamping device that is arranged in the skull connecting part, that has a clamping position and a release position, the bush clamping device in the clamping position being configured to fixate the shaft bush relative to the skull connecting part so that a direction of the bush channel axis relative to the central axis, which direction may be varied within a range of directions in the release position of the bush clamping device, is fixated as desired;
   an operating provision configured to engage the bush clamping device and to move the bush clamping device between the clamping position and the release position, the operating provision including at least:
      a first handle; and
      a second handle;
   the first and the second handles being configured and arranged to be engaged by a single hand and the operating provision being configured to bring the bush clamping device from the release position in the clamping position by movement of the first handle relative to the second handle, wherein the rotational position of the first handle and the second handle relative to the skull connecting part is settable without changing the position of the first handle relative to the second handle.

3. A shaft connector configured to connect a shaft that has to be partly inserted through the skull of patient to the skull of the patient, the shaft connector comprising:
   a skull connecting part having a proximal end and a distal end, the skull connecting part including:
      a skull connecting provision;
      an inner wall that bounds a skull connecting part channel that extends along a central axis and that has a distal channel end;
   a shaft bush that includes:
      a shaft bush wall defining a bush channel that extends along a bush channel axis;
   a bush clamping device that is arranged in the skull connecting part, that has a clamping position and a release position, the bush clamping device in the clamping position being configured to fixate the shaft bush relative to the skull connecting part so that a direction of the bush channel axis relative to the central axis, which direction may be varied within a range of directions in the release position of the bush clamping device, is fixated as desired;
   an operating provision configured to engage the bush clamping device and to move the bush clamping device between the clamping position and the release position, the operating provision including at least:
      a first handle;
      a second handle; and
      a third handle;
   the first and the second handles and the third handle and the second handles being configured and arranged to be engaged in pairs by a single hand and the operating provision being configured to bring the bush clamping device from the release position in the clamping position by movement of the first handle relative to the second handle, and to bring the bush clamping device from the clamping position in the release position by movement of the third handle relative to the second handle.

4. The shaft connector according to claim 3, wherein the rotational position of the first handle, the second handle and the third handle relative to the skull connecting part is settable without changing the position of the first handle, the second handle and the third handle relative to each other.

5. The shaft connector according to claim 3, wherein the second handle is positioned between the first handle and the third handle.

6. The shaft connector according to claim 1, the operating provision including:

a first operating part that is rotatably around the central axis and connected to the skull connecting part and that carries the first handle;
a second operating part that is rotatably around the central axis, independent of the first operating part, and connected to the skull connecting part and that carries the second handle;
the first operating part being moveable relative to the second operating part from a clamping position, that is associated with the clamping position of the operating provision, to the release position, that is associated with the release position of the operating provision, and vice versa.

7. The shaft connector according to claim 3, the operating provision including:
a first operating part that is connected to the skull connecting part and that carries the first handle;
a second operating part that is connected to the skull connecting part and that carries the second handle;
the first operating part being moveable relative to the second operating part from a clamping position, that is associated with the clamping position of the operating provision, to the release position, that is associated with the release position of the operating provision, and vice versa, wherein the first operating part carries the third handle.

8. The shaft connector according to claim 6, wherein both the first operating part and the second operating part are rotatable around the central axis relative to the skull connecting part so that the rotational position of the handles relative to the skull connecting part is settable.

9. The shaft connector according to claim 6:
the first operating part including a first ring that extends in a plane that is perpendicular to the central axis, the first ring having a central ring axis that coincides with the central axis,
the first ring having a first contact surface with a first sloping section;
the second operating part including a second ring that extends in a plane that is perpendicular to the central axis, the second ring having a central ring axis that coincides with the central axis;
the second ring having a second contact surface with a second sloping section, the first contact surface contacting the second contacting surface;
the first ring and the second ring being superimposed onto each other to form a ring set having a variable ring set height;
the ring set having a flat bottom surface that is in contact with the bush clamping device;
the ring set having a flat top surface that is positioned under a ridge of the skull connecting part;
the first sloping section and the second sloping section being positioned so relative to each other that these two sloping sections co-operate upon rotation of the first ring relative to the second ring thereby increasing or decreasing the ring set height.

10. A shaft connector configured to connect a shaft that has to be partly inserted through the skull of patient to the skull of the patient, the shaft connector comprising:
a skull connecting part having a proximal end and a distal end, the skull connecting part including:
a skull connecting provision;
an inner wall that bounds a skull connecting part channel that extends along a central axis and that has a distal channel end;
a shaft bush that includes:
a shaft bush wall defining a bush channel that extends along a bush channel axis;
a bush clamping device that is arranged in the skull connecting part, that has a clamping position and a release position, the bush clamping device in the clamping position being configured to fixate the shaft bush relative to the skull connecting part so that a direction of the bush channel axis relative to the central axis, which direction may be varied within a range of directions in the release position of the bush clamping device, is fixated as desired;
an operating provision configured to engage the bush clamping device and to move the bush clamping device between the clamping position and the release position, the operating provision including at least:
a first handle; and
a second handle;
the first and the second handles being configured and arranged to be engaged by a single hand and the operating provision being configured to bring the bush clamping device from the release position in the clamping position by movement of the first handle relative to the second handle, the operating provision including:
a first operating part that carries the first handle and that is connected to the skull connecting part and pivotable along a pivot axis that crosses and extends substantially perpendicular to the central axis, the first operating part including:
at least one cam surface that has an eccentric contour relative to the pivot axis and that engages the bush clamping device;
the pivot position of the first operating part along the pivot axis relative to the skull connecting part being settable by operating the first handle.

11. The shaft connector according to claim 1, the skull connecting part including:
a channel seat adjacent the distal channel end;
the shaft bush including:
a substantially spherical distal shaft bush end having a proximal side and a distal side;
the bush clamping device including:
a bush clamp provision that engages the proximal side of the substantially spherical distal shaft bush end in the clamping position and presses the spherical distal shaft bush end with the distal side thereof against the channel seat
an operating provision engagement part that is fixedly connected to the bush clamp provision;
the bush clamping device being movable in the direction of the central axis between the clamping position and the release position.

12. A shaft connector configured to connect a shaft that has to be partly inserted through the skull of patient to the skull of the patient, the shaft connector comprising:
a skull connecting part having a proximal end and a distal end, the skull connecting part including:
a skull connecting provision;
an inner wall that bounds a skull connecting part channel that extends along a central axis and that has a distal channel end;
a channel seat adjacent the distal channel end;
a shaft bush that includes:
a shaft bush wall defining a bush channel that extends along a bush channel axis;
a substantially spherical distal shaft bush end having a proximal side and a distal side;
a bush clamping device including:
an upper ring;
a lower ring;

spokes that fixedly connect the upper ring with the lower ring;
the bush clamping device being is arranged in the skull connecting part and being movable in the direction of the central axis between a clamping position and a release position, the bush clamping device in the clamping position being configured to fixate the shaft bush relative to the skull connecting part so that a direction of the bush channel axis relative to the central axis, which direction may be varied within a range of directions in the release position of the bush clamping device, is fixated as desired;
an operating provision configured to engage the bush clamping device and to move the bush clamping device between the clamping position and the release position, the operating provision including at least:
a first handle; and
a second handle;
the first and the second handles being configured and arranged to be engaged by a single hand and the operating provision being configured to bring the bush clamping device from the release position in the clamping position by movement of the first handle relative to the second handle, wherein the lower ring of the bush clamping device engages the proximal side of the substantially spherical distal shaft bush end in the clamping position and presses the spherical distal shaft bush end with the distal side thereof against the channel seat.

13. The shaft connector according to claim 1 including:
a shaft clamp that is configured to fixate a shaft within the shaft bush and configured to provide a release position and a clamping position.

14. The shaft connector according to claim 13, the shaft clamp thereof including:
a first shaft clamp handle; and
a second shaft clamp handle;
the first and the second shaft clamp handles being configured and arranged to be engaged by a single hand and the shaft clamp being configured to bring shaft clamp from the release position in the clamping position by movement of the first shaft clamp handle relative to the second shaft clamp handle.

15. A shaft connector configured to connect a shaft that has to be partly inserted through the skull of patient to the skull of the patient, the shaft connector comprising:
a skull connecting part having a proximal end and a distal end, the skull connecting part including:
a skull connecting provision;
an inner wall that bounds a skull connecting part channel that extends along a central axis and that has a distal channel end;
a shaft bush that includes:
a shaft bush wall defining a bush channel that extends along a bush channel axis;
a bush clamping device that is arranged in the skull connecting part, that has a clamping position and a release position, the bush clamping device in the clamping position being configured to fixate the shaft bush relative to the skull connecting part so that a direction of the bush channel axis relative to the central axis, which direction may be varied within a range of directions in the release position of the bush clamping device, is fixated as desired;
an operating provision configured to engage the bush clamping device and to move the bush clamping device between the clamping position and the release position, the operating provision including at least:
a first handle; and
a second handle;
the first and the second handles being configured and arranged to be engaged by a single hand and the operating provision being configured to bring the bush clamping device from the release position in the clamping position by movement of the first handle relative to the second handle;
a shaft clamp that is configured to fixate a shaft within the shaft bush, the shaft clamp including:
a first shaft clamp handle; and
a second shaft clamp handle;
a third shaft clamp handle;
the first and the second shaft clamp handles and alternatively the first and the third shaft clamp handles being configured and arranged to be engaged by a single hand and the shaft clamp being configured to bring the shaft clamp from the release position in the clamping position by movement of the first handle relative to the second handle, and to bring the shaft clamp from the clamping position in the release position by movement of the third shaft clamp handle relative to the first shaft clamp handle.

16. The shaft connector according to claim 15, wherein the rotational position of the first shaft clamp handle, the second shaft clamp handle and the third shaft clamp handle relative to the shaft bush is settable without changing the position of the first handle, the second handle and the third handle relative to each other.

17. A shaft connector configured to connect a shaft that has to be partly inserted through the skull of patient to the skull of the patient, the shaft connector comprising:
a skull connecting part having a proximal end and a distal end, the skull connecting part including:
a skull connecting provision;
an inner wall that bounds a skull connecting part channel that extends along a central axis and that has a distal channel end;
a shaft bush that includes:
a shaft bush wall defining a bush channel that extends along a bush channel axis;
a bush clamping device that is arranged in the skull connecting part, that has a clamping position and a release position, the bush clamping device in the clamping position being configured to fixate the shaft bush relative to the skull connecting part so that a direction of the bush channel axis relative to the central axis, which direction may be varied within a range of directions in the release position of the bush clamping device, is fixated as desired;
an operating provision configured to engage the bush clamping device and to move the bush clamping device between the clamping position and the release position, the operating provision including at least:
a first handle; and
a second handle;
the first and the second handles being configured and arranged to be engaged by a single hand and the operating provision being configured to bring the bush clamping device from the release position in the clamping position by movement of the first handle relative to the second handle, the shaft clamp including:
an inner tapering wall part with a diminishing diameter that is defined by the shaft bush wall adjacent the proximal end of the shaft bush, wherein the diminishing diameter of the inner tapering wall part diminishes when viewed from a proximal end to a distal end of the shaft bush wall;

a clamp bush with a clamp bush wall defining a clamp bush channel that extends along bush channel axis;

slits in the clamp bush wall that extend substantially parallel to the bush channel axis;

a distal end of the clamp bush wall defining shaft clamping segments that are bounded by the slits, the clamping segments having radial inwardly directed clamping surfaces that are configured to engage a shaft;

a radial outwardly directed clamp bush wall part at the distal end of the clamp bush wall co-operating with the inner tapering wall part;

the clamp bush being arranged axially moveable within the shaft bush wall;

a clamp bush operating provision being provided to control the axial position of the clamp bush relative to the shaft bush wall and including at least the first and the second shaft clamp handle.

18. The shaft connector according to claim 17, the clamp bush operating provision including:

a cam notch that is axially fixed relative to the shaft bush wall;

a cam surface that is part of the clamp bush and that is configured to co-operate with the cam notch so that a rotation of the clamp bush relative to the cam notch results in an axial movement of the clamp bush.

19. The shaft connector according to claim 18, including:

a notch ring that is connected to the shaft bush wall so that it is axially fixed relative to the shaft bush wall and rotatable around the shaft bush wall and that carries the cam notch, the first shaft clamp handle being connected to the notch ring;

a clamp bush skirt that extends parallel to the clamp bush wall and that is connected to the clamp bush wall via a connecting flange, the clamp bush skirt carrying the cam surface, the second shaft clamp handle being connected to the clamp bush skirt.

20. The shaft connector according to claim 1, the skull connection provision including:

a substantially cylindrical part extending proximally from the distal end of the skull connecting part; and a stop surface at a proximal end of the substantially cylindrical part and extending substantially perpendicular to the central axis.

21. The shaft connector according to claim 20, including:

outer screw thread on the cylindrical part configured to engage a hole in the skull.

22. The shaft connector according to claim 20, the skull connecting part including:

an outer surface wall that is circular symmetric around the central axis and extends from a proximal end of the cylindrical part substantially parallel to the central axis in the proximal direction and diverges radial outwardly, thus providing a concave transition zone that is configured to accommodate skin on the skull that surrounds the hole in which the skull connecting part may be mounted.

23. The shaft connector according to claim 11, the skull connection provision including:

a substantially cylindrical part extending proximally from the distal end of the skull connecting part;

the seat being at a distal end of the cylindrical part; and the substantially spherical distal shaft bush end being positioned in the cylindrical part.

24. The shaft connector according to claim 1, wherein the shaft bush includes:

a substantially spherical distal shaft bush end that is pivotably accommodated in the skull connecting part so that the shaft bush is pivotable relative to the skull connecting part, the substantially spherical distal shaft bush end being positioned adjacent the distal channel end of the skull connecting part so that in a mounted position of the skull connecting part in a hole in a skull, the substantially spherical distal shaft bush end is positioned below an outer surface of skull.

* * * * *